(12) United States Patent
Hamel et al.

(10) Patent No.: US 8,080,024 B2
(45) Date of Patent: Dec. 20, 2011

(54) PROTECTIVE ENCLOSURE FOR MEDICAL DEVICE COMPONENTS

(75) Inventors: Kory P. Hamel, Bloomington, MN (US); Vincent G. Copa, Minnetonka, MN (US); Sidney F. Hauschild, St. Paul, MN (US)

(73) Assignee: AMS Research Corporation, Minnetonka, MN (US)

( * ) Notice: Subject to any disclaimer, the term of this patent is extended or adjusted under 35 U.S.C. 154(b) by 654 days.

(21) Appl. No.: 11/116,505

(22) Filed: Apr. 28, 2005

(65) Prior Publication Data

US 2006/0247666 A1    Nov. 2, 2006

(51) Int. Cl.
*A61B 17/08*      (2006.01)
*A61B 17/00*      (2006.01)
*A61B 17/06*      (2006.01)
*A61M 27/00*     (2006.01)
*B65D 83/10*      (2006.01)

(52) U.S. Cl. ............ 606/153; 606/1; 604/544; 206/363; 206/438

(58) Field of Classification Search .................. 606/151, 606/153, 139–150, 167–180, 191–194, 205–211, 606/1; 369/13.36, 13.37; 439/367; 280/93.515; 604/164.04, 540–545, 164.08, 236, 192–198; 206/363, 438, 437, 305, 570, 493; 340/870.1, 340/683, 724; 600/437, 101–183; 174/66
See application file for complete search history.

(56) References Cited

U.S. PATENT DOCUMENTS

| | | | | |
|---|---|---|---|---|
| 3,749,301 A * | 7/1973 | Peckar | ..................... | 229/125.37 |
| 3,752,309 A * | 8/1973 | Hopkins et al. | ............... | 206/306 |
| 3,818,903 A * | 6/1974 | Bleecker | ..................... | 604/98.01 |
| 4,140,127 A * | 2/1979 | Cianci et al. | ................... | 604/171 |
| 4,227,534 A * | 10/1980 | La Rosa | ..................... | 604/98.02 |
| 4,946,449 A * | 8/1990 | Davis, Jr. | ....................... | 604/256 |
| 4,976,692 A * | 12/1990 | Atad | .......................... | 604/101.03 |
| 5,041,092 A * | 8/1991 | Barwick | ........................ | 604/104 |
| 5,271,379 A * | 12/1993 | Phan et al. | .................... | 600/104 |
| 5,441,152 A * | 8/1995 | Estes | .............................. | 206/570 |
| 5,474,179 A * | 12/1995 | Iosif et al. | ...................... | 206/363 |
| 5,534,221 A * | 7/1996 | Hillebrenner et al. | .......... | 422/33 |
| 5,695,491 A * | 12/1997 | Silverstein | ........................ | 606/1 |
| D421,217 S * | 2/2000 | Discko, Jr. | ..................... | D9/723 |
| 6,162,201 A * | 12/2000 | Cohen et al. | ................... | 604/250 |
| 6,258,060 B1 * | 7/2001 | Willard | .......................... | 604/117 |
| 6,405,863 B1 * | 6/2002 | Dhindsa | ......................... | 206/370 |
| 6,638,253 B2 * | 10/2003 | Breznock | ................. | 604/164.04 |
| 6,926,151 B1 * | 8/2005 | Perry et al. | ..................... | 206/750 |
| 7,052,493 B2 * | 5/2006 | Vaska et al. | ..................... | 606/41 |
| 7,695,814 B2 * | 4/2010 | Gartstein et al. | .............. | 428/407 |
| 7,708,720 B1 * | 5/2010 | Angstrom et al. | ............. | 604/263 |
| 2001/0040110 A1 * | 11/2001 | Ye et al. | ......................... | 206/363 |
| 2004/0087995 A1 * | 5/2004 | Copa et al. | ..................... | 606/192 |
| 2005/0061698 A1 * | 3/2005 | Delaney et al. | ............... | 206/364 |
| 2005/0070938 A1 | 3/2005 | Copa et al. | | |
| 2005/0131431 A1 | 6/2005 | Copa et al. | | |
| 2006/0086634 A1 * | 4/2006 | Steppe | .......................... | 206/438 |
| 2006/0264822 A1 * | 11/2006 | Nagamatsu | ................ | 604/97.02 |

* cited by examiner

*Primary Examiner* — Corrine M McDermott
*Assistant Examiner* — Dianne Dornbusch
(74) *Attorney, Agent, or Firm* — Kimberly K. Baxter; Gregory L. Koeller

(57) ABSTRACT

An anastomosis surgical device comprising an elongate body having a drainage aperture at a distal end for communication with a proximal end of the elongate body, tissue approximating structure extendable from the elongate body and spaced proximally from the drainage aperture along the length of the elongate body. The device further includes an actuating mechanism extending from the proximal end of the elongate body and comprising at least one tissue approximating structure control mechanism, and a protective enclosure surrounding at least a portion of the actuating mechanism.

19 Claims, 3 Drawing Sheets

PROTECTIVE ENCLOSURE FOR MEDICAL DEVICE COMPONENTS

TECHNICAL FIELD

The invention relates generally to devices for protecting components of a medical device that extend outside the patient's body. More specifically, the invention relates to protecting the components that extend outside the patient's body of devices used for performing anastomosis procedures, including urethral procedures that involve reconnecting urethra and bladder tissues after a radial prostatectomy, vesico-urethral anastomosis, and end-to-end urethral anastomosis.

BACKGROUND OF THE INVENTION

Anastomosis procedures are required for connecting or re-connecting body tissue, e.g., as part of a surgical procedure. The tissue may be part of a body lumen such as a blood vessel, intestinal or other digestive system tissue, or tissue relating to the urinary system. As one example, in a radical prostatectomy, a surgeon removes all or most of a patient's prostate. Because the urethra travels through the prostate immediately before reaching the bladder, the upper part of the urethra is also removed with the surgery. The procedure leaves a severed urethral stump and a severed bladder neck. To restore proper urinary functions, the bladder and the urethra must be reconnected.

Conventionally, a surgeon may execute delicate suturing operations with tiny, fine needles to reconnect these or other anatomical bodies. However, installation of sutures with a needle to connect severed tissues can be a difficult and technique-sensitive task. Many factors can make the task difficult, including a very small amount of tissue to work with (e.g., at the urethral stump and at the bladder neck), and proximal sensitive tissues such as ureters at a bladder and a proximal nerve bundle and sphincter at a urethral stump. These factors result in complicated and delicate suturing procedures that, if not performed properly, could result in complications such as leakage, difficulty in healing or failure to heal, or specific conditions such as incontinence or impotence. Specific problems that can occur include necrosis of the sutured tissues; stricture of the urethra, which impedes the flow of fluid through the urethra; and a urethra-bladder connection that is not fluid-tight. In addition, methods of suturing the urethra to the bladder allow for the possibility of accidental or inadvertent piercing of the nearby neurovascular bundle, which can cause incontinence or impotence.

To reduce the risks involved in conventional suturing procedures, anastomosis devices have been developed that include features that allow for reconnection of tissues without using traditional sutures. These anastomosis devices eliminate the need for sutures to reconnect severed tissue during anastomosis procedures, which can both reduce the risks during the surgical procedure and also provide a significant reduction in the amount of time required to perform certain anastomosis procedures. When an anastomosis device of this type is surgically positioned with the tissue approximating structure inside the patient, its actuating mechanism can be attached to the device and located outside the patient's body, where the surgeon or doctor can manipulate it via some type of control device or mechanism, as desired. In some cases, this configuration of the actuating mechanism may also allow for inadvertent or purposeful manipulation of the externally located components by the patient after the surgeon properly positions the device and actuates the tissue approximating structures. Any such manipulation of the actuating mechanism can be somewhat undesirable for the recovery of the patient, such as if a patient were to retract the tines before the reconnection of tissues within the body has taken place. In this case, the tissues may not heal completely, which can cause a variety of physical issues for the patient, such as leakage of bodily fluids in the area where a urethra-bladder connection is not fluid-tight. Thus, it may be desirable in some cases to prevent or limit intentional and unintentional manipulation of the actuating mechanism for the external actuating mechanisms and associated componentry of an anastomosis device.

SUMMARY OF THE INVENTION

Examples of anastomosis devices that include a drainage feature and tissue approximating structure that allow for reconnection of tissues without using traditional sutures are described, for example, in Applicants' co-pending United States patent applications having Ser. No. 10/646,383, filed Aug. 21, 2003, entitled "Anastomosis Device and Related Methods"; Ser. No. 10/919,545, filed Aug. 16, 2004, entitled "Anastomosis Device and Related Methods"; and Ser. No. 10/919,775, filed Aug. 16, 2004, entitled "Anastomosis Device and Related Methods", all of which are incorporated herein by reference in their entireties. Anastomosis devices of the type described above can include an elongated body, tissue approximating structure that extends from the elongated body, such as one or multiple sets of tines, mechanisms for actuating the tissue approximating structure, a drainage lumen that may extend as a channel within the length of the elongated body and that communicates at its distal end with a drainage aperture, and a balloon at or adjacent to the distal end of the device. The actuating mechanisms for the tissue approximating structure are located generally at a proximal end of the device and may include any of a wide variety of actuation configurations that would provide for extension and retraction of the tissue approximating structure, as desired.

The invention relates to anastomosis devices that include such external componentry that is connected to or in communication with mechanisms such as tissue approximating structures for reconnecting severed tissue in a patient. Examples of external componentry that may be a part of the anastomosis device include an actuating mechanism having control devices such as knobs, levers, or the like. In particular, the invention includes a protective enclosure that can advantageously protect the actuating mechanism and its control devices from being manipulated while the device is in its surgically installed position. In addition, the protective enclosure can protect the actuating mechanism itself from being damaged by the patient during the healing process. Yet another advantage provided by the use of a protective enclosure is that it allows greater latitude in designing the external componentry of the anastomosis device because the enclosure can be used to cover rigid or sharp-edged componentry that would otherwise be undesirable to leave exposed to the patient.

According to one aspect of the invention, an anastomosis device is provided which comprises an elongate body having a drainage aperture at a distal end for communication with a proximal end of the elongate body, tissue approximating structure extendable from the elongate body and spaced proximally from the drainage aperture along the length of the elongate body, an actuating mechanism extending from the proximal end of the elongate body and comprising at least one tissue approximating structure control mechanism, and a protective enclosure surrounding at least a portion of the actuating mechanism. The protective enclosure may include first and second body portions that can be attached to each other by a hinge and may include a closure mechanism for maintaining the protective enclosure in a closed position. The protective enclosure comprises may include a relatively rigid outer surface surrounding an inner cavity, wherein at least a portion of the actuating mechanism is positionable within the inner cavity of the protective enclosure. Alternatively, the protective enclosure may include a flexible material that is conformable to at least some of the outer surfaces of the actuating mechanism, such as an elastically deformable material. To maintain the protective enclosure in its closed position, it may further include a locking mechanism.

BRIEF DESCRIPTION OF THE DRAWINGS

The invention will be further explained with reference to the appended Figures, wherein like structure is referred to by like numerals throughout the several views, and wherein.

DETAILED DESCRIPTION

Figure 1:
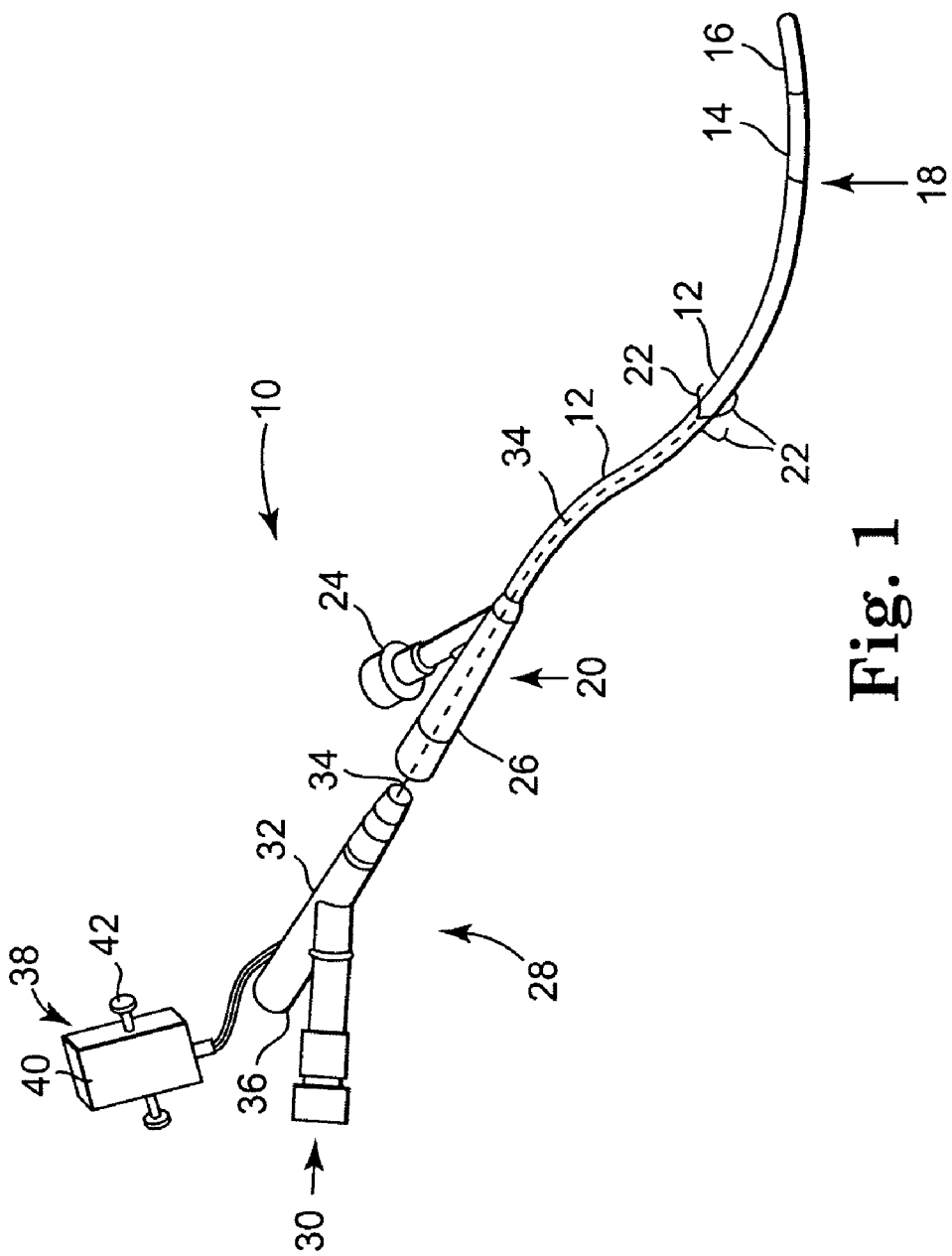
FIG. 1 is a perspective view of an exemplary anastomosis device including an actuating mechanism for tissue approximating structures.

Referring now to the Figures, wherein the components are labeled with like numerals throughout the several Figures, and initially to FIG. 1, one exemplary configuration of a modified Foley catheter-type anastomosis device 10 is illustrated. Device 10 includes a catheter body 12, a distal end portion 18, a proximal end portion 20, a balloon 14, and a drainage aperture 16 located near the distal end of device 10. In many ways, this modified anastomosis device has a similar structure to that of a standard Foley catheter, which typically includes a thin, sterile tube that is inserted into the patient's bladder to drain urine. These catheters are held in place for a period of time by a balloon at one end that is filled with sterile water to hold it in place in the patient's body. Urine can enter the tube through a drainage aperture located adjacent to the balloon, which then drains into a bag that is located outside the patient's body. This bag can periodically be emptied, as necessary, after which the urine can be discarded, sent to a laboratory for analysis purposes, or otherwise transported from the device. Anastomosis device 10 of FIG. 1 works similarly, but further includes tissue approximating structure or structures 22 spaced from balloon 14 along the length of catheter body 12, such as at a position approximately halfway between distal and proximal end portions 18, 20 of catheter body 12.

Tissue approximating structure 22 of device 10 can be any type of device or structure that can be used to cause contact between severed tissues, such as to cause contact between severed urethral tissues, or such as to cause contact between severed tissue of the bladder or bladder neck and severed tissue of the urethral stump or perineal floor, and can additionally hold these surfaces in contact with each other throughout a patient's healing process. The tissue approximating structure may include, for example, one or multiple balloon or balloon-like structures that can be placed against the inside of the bladder or underneath the perineal floor to bring severed bladder neck tissue into contact with a severed tissue surface of the urethral stump. Alternatively, the tissue approximating structure may include elongate structures such as needles, tines, prods, probes, or the like, each of which may have a blunt or a sharp end and may movably extend or protrude from an aperture in the flexible catheter body 12 at a location where the structure can function as an approximating structure. For example, the tissue approximating structure can extend from an area near the distal end of the device if the structure will be near the bladder or perineal wall when installed or if the structure will be at or near a severed urethra below the perineal floor when installed. Alternatively, combinations of balloons and elongate structures may be used as the tissue approximating structures in certain applications. The inclusion of tissue approximating structure 22 in anastomosis device 10 preferably limits or excludes the need for a surgeon to use internal sutures, thereby eliminating or limiting the need to use any components or structures designed to function in combination with a suture or suturing device, such as a needle.

FIG. 1 illustrates one of many possible configurations for the tissue approximating structure 22 of anastomosis device 10. As shown, one exemplary embodiment of tissue approximating structure 22 includes multiple sharp elongate metal tines that can extend from and retract into catheter body 12 at a location that allows contact and optional penetration of adjacent tissue structures. For example, the tissue approximating structure can be positioned within a patient to allow contact and optional penetration of the urethral stump proximal tissue in the adjacent perineal floor, urethra, or bulbar urethra. In this example, elongate tissue approximating structure 22 may serve the dual purpose of causing contact between the severed tissue surfaces of the urethral stump and the bladder neck, along with the desirable effect of re-exposing the urethral stump from the perineal floor by pressuring the urethral stump from below, which can help prevent the tendency of the small amount of tissue associated with the urethral stump to draw into the perineal floor.

Tissue approximating structure 22 may specifically include two sets of elongated structures, which may optionally be deployable or otherwise moveable in opposite directions from each other. More directional capabilities are possible; such as if more than two tissue approximation structures are used. In any case, the elongated structures may be rigid or semi-rigid tines, needles, or the like, which may be straight or curved, and which may optionally include a sharp pointed tip to penetrate into or through a bladder neck, bladder wall, perineal floor, urethra tissue, bulbar urethra, urethral stump, or any other tissue that can be brought into contact or held together by devices or methods described herein. For example, the anastomosis device may include a first or distal set of tissue approximating structures 22 located on the proximal side of the balloon and positioned to extend through apertures in the hollow catheter body 12. Device 10 may further include a second or proximal set of tissue approximating structures 22 that are similarly positioned to extend through apertures in hollow catheter body 12 and that are located on the proximal side of the moveable distal set of tissue approximating structures. Each of the two sets of tissue approximating structures can be extendable at the same time or may be controllable independently and remotely relative to each other, such as through the operation of an actuating mechanism. A wide variety of actuating mechanisms may be used, such as a wire or shaft connected to the tissue approximating that runs through or along the length of the catheter body, some examples of which will be described in further detail below.

Referring again to FIG. 1, proximal end portion 20 of the anastomosis device 10 comprises a main body portion 26 that extends from proximal end area of catheter body 12. Proximal end configurations of the type shown are well known, and such known or future developed proximal ends and attachments are understood to be included within the scope of the invention. Main body portion 26 extends generally in the direction of the length of catheter body 12 and may be at least slightly wider than catheter body 12. A port 24 extends or protrudes from main body portion 26 and may connect to a lumen (not shown) such as an inflation lumen for balloon 14 or a drainage lumen extending from drainage aperture 16. Device 10 further includes another attachment or extension 28 that extends from the end of the main body portion 26 that is opposite the end attached to catheter body 12. This extension 28 includes a port 30 that extends or protrudes from a main body portion 32. Port 30 may also be used with a lumen such as an inflation lumen for balloon 14 or a drainage lumen extending from drainage aperture 16. Extension 28 is preferably attached to main body 26 of proximal end portion 20 in a snap-fit configuration; however, extension 28 may instead be configured for attachment to main body 26 in some other way, such as with threaded portions or other mechanical attachment, or with an adhesive or the like. Alternatively, proximal end portion 20 and extension 28 may be molded together as a single piece construction, which piece may then include one or both of the ports 24 and 30 extending from the single extension piece or may include additional ports, if desired.

Device 10 also includes an actuating wire 34 that extends through the interior portion of catheter body 12, such as within the wall of body 12 or within an open channel through catheter body 12. Actuating wire 34 is attached to an actuating mechanism 38 that is used for extending and retracting tissue approximating structure 22. As shown, actuating wire 34 extends generally along the length of catheter body 12 from tissue approximating structure 22, through proximal end portion 20, and into body portion 32 of extension 28. Actuating wire 34 preferably also extends through the side of main body portion 32 of extension 28 adjacent to a proximal end 36 of main body portion 32. Actuating wire 34 then communicates or is attached to actuating mechanism 38, one exemplary embodiment of which is illustrated as extending from main body portion 28.

Although actuating wire 34 is illustrated as a single wire, actuating wire 34 may instead include a series or bundle of wires that each activate one set or more than one set of tissue approximating structures. Further, actuating wire 34 may not actually be a wire, but may instead have a different structure or configuration, depending on the tissue approximating structure used. That is, if the tissue approximating structure is actuated by a mechanism other than a wire, (e.g., fluid or air pressure), a corresponding actuating device or structure will be used instead of an actuating wire or wires. For one specific example, actuating wire 34 of FIG. 1 may instead take the configuration of a tube if the corresponding tissue approximating structure is an inflatable balloon. Further, it is contemplated that the tissue approximating structure or structures can be attached to an actuating mechanism in a number of different ways, depending on the configuration of the tissue approximating structures and the corresponding devices or structures used for activation of those tissue approximating structures.

Actuating mechanism 38 comprises a main body 40 and two extending control knobs 42. The internal componentry (not shown) within main body 40 may include a wide variety of configurations, but generally involves a connection of the mechanism (e.g., actuating wire 34) from the tissue approximating structures to the control mechanism or mechanisms (e.g., control knobs 42) of the actuating mechanism. Actuating mechanism 38 may include external control devices or mechanisms that are different than the illustrated control knobs, such as levers, pins, buttons, or the like, which are able to be physically manipulated to maneuver the tissue approximating structures.

An anastomosis surgical device of the type described herein can remain installed in the patient throughout the time required for healing of the two tissue surfaces together. During this time, the balloon of the device typically remains inflated within the patient's bladder to prevent urine from passing through the bladder neck. The healing period can be considered to be the time period taken for severed tissue to achieve a watertight anastomosis. The healing period can depend on many factors, such as the type of operation and condition of the patient, and can take from possibly as little as one or two days up to two months or more, where periods of about two to four weeks would be somewhat typical lengths for healing periods. The use of the anastomosis devices described with respect to the invention thus offer the advantage of allowing the tissue approximation structures to position and maintain the severed tissues in contact with each other during healing, thereby eliminating the need for the extra time and complications that would be involved with suturing the tissues, while at the same time providing a draining mechanism. During this healing period, it is desirable for the tissue approximation structures to remain fixed within the tissues of the patient. Only when the healing is complete should the tissue approximating structures be retracted from the tissues of the patient. The balloon can also be deflated at this time so that the device can be removed from the patient. Thus, a protection mechanism may be provided in accordance with the invention to help prevent undesirable movement of the tissue approximating structures prior to the completion of the healing process.

Figure 2:
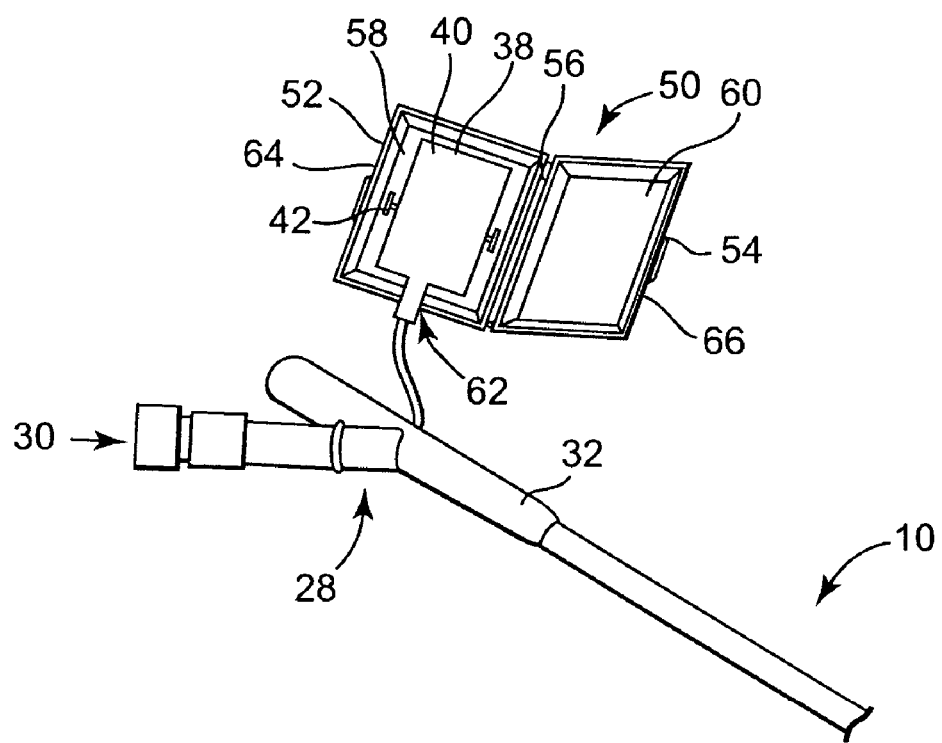
FIG. 2 is a perspective view of a portion of the anastomosis device of FIG. 1, further including one exemplary protective enclosure for the actuating mechanism, with the enclosure in an open position.

Referring now to FIG. 2, one exemplary embodiment of a protective enclosure 50 is shown in its open position, along with a portion of device 10 that generally includes extension 28 and its main body portion 32, port 30, and actuating mechanism 38 positioned within a portion of enclosure 50. Protective enclosure 50 includes a first body portion 52 connected to a second body portion 54 by a hinge 56. First body portion 52 includes a recessed inner compartment 58, and second body portion 54 includes a recessed inner compartment 60. Inner compartments 58, 60 are sized and shaped to enclose at least a portion of actuating mechanism 38 and in particular are sized and shaped to enclose any elements of actuating mechanism 38 that may be manipulated to control tissue approximating structures. Thus, in this embodiment, inner compartments 58, 60 are sized and shaped to enclose the main body 40 of the actuating mechanism along with its extending control knobs 42.

An opening 62 is provided at the bottom area of the protective enclosure 50 to accommodate any extending actuating wires or other components that operatively connect the actuating mechanism 38 to the device 10. The opening 62 should be large enough that the actuating wires or components are not damaged when the enclosure 50 is in its closed position. First and second body portions 52, 54 each further include an edge 64, 66, respectively, which extend generally around the perimeter of their respective first and second body portions 52, 54, except in the area of opening 62. These edges 64, 66 are complimentary surfaces that provide a relatively close fit when in contact with each other in order to provide a seal that can further protect an enclosed actuating mechanism from contaminants. Thus, the surfaces of first and second body portions 52, 54 that come in contact with each other when the enclosure 50 is closed are preferably designed to match or mate with each other when the enclosure is closed. In one embodiment, the edges 64, 66 are simply flat surfaces. Flexible gaskets or sealing members may be provided around all or part of the perimeter of the enclosure along one or both edges 64, 66 to further effect the ability of the enclosure to protect any mechanisms that are enclosed therein.

Figure 3:
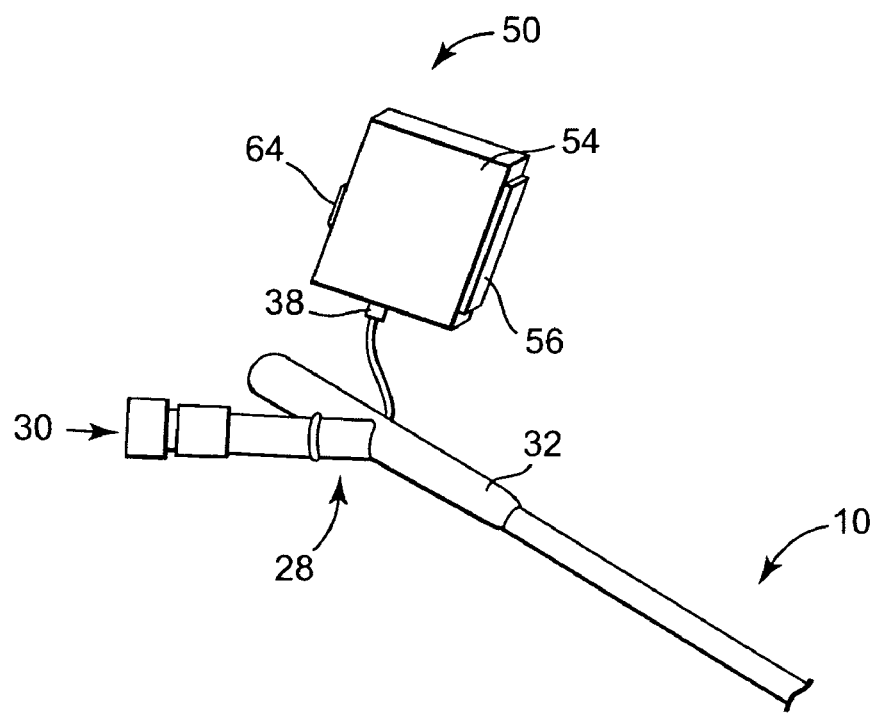
FIG. 3 is a perspective view of the portion of the anastomosis device of FIG. 2, with the protective enclosure shown in its closed position.

FIG. 3 illustrates the protective enclosure 50 of FIG. 2 in its closed position. As shown, the second body portion 54 was rotated about hinge 56 to contact the first body portion (not visible), thereby providing an enclosed inner compartment or cavity that covers and protects the actuating mechanism of device 10. That is, inner compartment 58 of first body portion 52 and inner compartment 60 of second body portion 62 together provide a single inner compartment when the enclosure 50 is closed. This inner compartment is preferably just slightly larger in size than the actuating mechanism it encloses, in order to not substantially increase the size of the componentry outside the patient. However, the enclosure and its inner cavity may alternatively only be large enough to cover or surround a portion or portions of the actuation mechanism, such as its control mechanisms and/or a portion of its main body.

Enclosure 50 further includes a clasp or closure 64 that provides for a positive engagement between the first and second body portions 52, 54, when the enclosure is in its closed configuration, thereby keeping the first body portion 52 and second body portion 54 from moving relative to each other. It is further desirable that the positive engagement of the clasp 64 is sufficient to keep the enclosure 50 in its closed position throughout normal movements of the patient in which the device 10 is installed.

One exemplary embodiment of clasp 64 includes a tab portion extending from first body portion 52 that positively engages with an opening or receiver-portion that extends from second body portion 54. However, clasp 64 may instead include a wide variety of alternative configurations that can hold the first and second body portions 52, 54 together. For example, first and second body portions 52, 54 may include various types of complementary devices that engage with each other by mechanical engagement, adhesive engagement, magnetic attraction, frictional attraction, or the like. The amount of attraction or engagement between the two portions can be chosen and designed depending on the desired level of protection for an enclosed actuating device. That is, in cases where it is likely that the patient will have limited mobility during the healing process and/or in cases where intentional or unintentional manipulation of the actuating device would be relatively unlikely, the level of attraction or engagement between body portions of the protective enclosure can be relatively minimal. In contrast, in cases where it is likely that the patient will be relatively active during the healing process and/or in cases where intentional or unintentional manipulation of the actuating device would be more likely to occur, the level of attraction or engagement can be relatively strong between the two portions of the enclosure.

Other examples of mechanisms for keeping first and second body portions 52, 54 in a closed configuration include using materials such as hook and loop type fasteners, which generally comprise a loop fabric on one surface that can engage with hooks on a mating surface to secure the two surfaces together. Any portion or portions of first and second body portions 52, 54 that come in contact with each other when enclosure 50 is closed can include such engageable hook and loop type materials. For example, rather than using an separate closure structure, such as clasp 64, device 50 may instead include a hook and loop type fastener along the edges 64, 66 or a portion of the edges 64, 66 of first and second body portions 52, 54. Hook and loop type fasteners, as used with the invention, may include a wide variety of arrangements, including those that are in a specifically designed and ordered arrangement, or those that are more irregular and random, such as mating materials that can "snag" or otherwise engage with each other.

Another material that can similarly be used to secure first and second body portions 52, 54 to each other when enclosure 50 is in its closed position includes intermeshed structured surfaces that engage with each other to attach the two surfaces together. An example of such structured surfaces include a plurality of tapered elements on one surface that can frictionally engage with tapered elements on another surface with which it will come in contact. As mentioned above, first and second body portions 52, 54 can alternatively be held in contact with each other through the use of magnetic attraction, which can specifically include a ferromagnetic material on one surface of enclosure 50 that is attracted to a magnetized material on another surface of enclosure 50. If such magnetic attraction is the securing configuration that is used, the ferromagnetic material may be coated or positioned as a separate layer on the appropriate enclosure surface, or it may instead be incorporated directly into the material from which the enclosure is constructed.

With the different securing devices and configurations described herein, the engaging materials and/or structures can be positioned at any desired location on the enclosure that provides for a sufficiently secure closure. That is, the materials or structures can be located along at least some portion of the edge of the enclosure that is opposite the edge including the hinge, on one or both edges of the enclosure that are adjacent to the edge including the hinge, along the edge that includes the hinge, or some combination of these various surfaces. Further, it is possible for a single enclosure, such as enclosure 50, to include more than one different kind of configuration for maintaining the enclosure in its closed position when an activating mechanism is contained within it. It is also possible that the securing configuration includes components or structures located within the interior portion of one or both of first and second body portions 52, 54 that engage with each other. For example, such a configuration can include a hollow tube that extends from one of the body portions that can accept a mating post from an opposing body portion. The post may snap into the tube, or the post can frictionally engage with the inside surfaces of the tube, for example. Thus, it is understood that a wide variety of devices and/or configurations may be used to secure first and second body portions 52, 54 in the closed position of protective enclosure 50.

A locking mechanism or device may be used in combination with a particular configuration of the clasp 64 or other closure configuration to further keep the first and second body portions 52, 54 in contact with each other in the closed position of protective enclosure 50. The locking mechanism may include a device that requires either a small or large amount of effort to be defeated by the patient to open the enclosure 50. For one example, if the locking mechanism is incorporated into the clasp or closure in the form of magnetic attraction between two clasp pieces, the locking mechanism could be defeated by the patient by simply pulling first and second body portions 52, 54 away from each other to break the magnetic bond between the pair of clasp portions. The device can alternatively be designed so that some type of tool or device is necessary to break the magnetic attraction, particularly when the level of the magnetic attraction is high. For another example, the locking mechanism may be configured such that it can only be opened with a specially designed tool that disconnects or unlocks the clasp pieces from each other. In yet another example, the locking mechanism may include a combination or key that is not made available to the patient. It is noted that any locking mechanism used is preferably designed to further minimize or prevent accidental opening of the protective enclosure, but may additionally be designed to prevent intentional opening of the protective enclosure, such as to prevent a patient from tampering with an enclosed actuating mechanism.

Protective enclosure 50 may be made of a variety of materials, where the selection of materials can again depend on the desired protection for an actuating device that will be enclosed therein. For example, protective enclosure 50 may be designed for relatively robust protection and thus can be made of a metal, a plastic material that is rigid or semi-rigid, or other relatively hard covering material. However, it is also desirable that enclosure 50 be relatively lightweight and as small in size as possible. Thus, the material and the thickness of the material should be chosen to meet the strength standards for the enclosure 50; however, the material and the thickness of the material should not be so large that it makes the enclosure too heavy or unwieldy.

Protective enclosure 50 is described above as including two portions 52, 54 that are attached to each other at hinge 56; however, a protective enclosure may instead include separate pieces that are not secured to each other in any way until they are used to cover at least a portion of the actuating mechanism. That is, two or more mating enclosure portions can be independent pieces that are pressed or otherwise secured to each other around the actuating mechanism. It is further understood that a protective enclosure of the invention may be more integrated into the anastomosis device itself, such as if no wires or other devices extend from the elongated body to the actuating mechanism (i.e., the actuating mechanism is integrated directly into the elongated body). In this case, the protective enclosure may optionally extend directly from the elongated body and/or may be permanently attached to the actuating mechanism.

Figure 4:
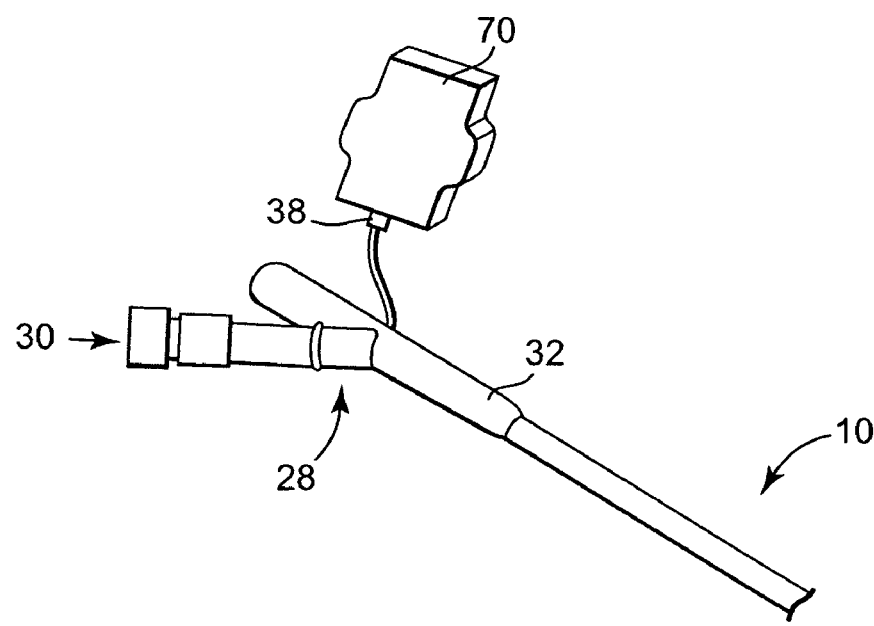
FIG. 4 is a perspective view of a portion of the anastomosis device of FIG. 1, further including another exemplary protective enclosure for the actuating mechanism.

FIG. 4 illustrates another exemplary embodiment of a protective enclosure 70, shown with a portion of device 10 that generally includes extension 28 and its main body portion 32, port 30, and actuating mechanism 38 (not visible). Protective enclosure 70 is shaped to closely follow the contours of the enclosed actuating mechanism, thereby minimizing the size of enclosure 70. To accomplish this, enclosure 70 may be molded or formed from a rigid or semi-rigid material, such as plastic, to match the outer configuration of actuating mechanism 38. Thus, a particular enclosure may only be useful for protecting one or a few configurations of actuating mechanisms. Alternatively, enclosure 70 may be made of a relatively flexible material that can slip over an actuating mechanism and generally mold or conform to the outer contours of that actuating mechanism. In this case, enclosure 70 may be made of a cloth or other relatively thin, flexible material, which may be somewhat elastic, if desired. In this way, it can stretch to cover the outer contours and mechanisms of its enclosed actuating mechanism. Examples of flexible materials from which the enclosure can be made include neoprene, flexible rubberized cloth, rubber, and the like. While this type of flexible enclosure may not provide the same level of protection against impact or other manipulation as an enclosure made of a harder or more rigid material, an enclosure that is made of a more flexible material advantageously can provide a barrier to manipulation of the enclosed actuating mechanism while minimizing the size and weight of the enclosure.

The protective enclosures of the present invention, such as enclosures 50 and 70 described above, can also be used for to protect external communication devices of anastomosis surgical devices other than or in addition to the external controls for tissue approximating structures. For example, a protective enclosure may be used to protect the inflation port pf an anastomosis device from intentional or unintentional manipulation by the patient. In addition, a protective enclosure of the invention may be provided for devices used with techniques such as dialysis or catheterization in order to prevent or minimize manipulation of external controls.

The invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the invention should not be limited to the structures described herein, but only by the structures described by the language of the claims and the equivalents of those structures.

The invention claimed is:

1. An anastomosis surgical device comprising:
an elongate body having a drainage aperture at a distal end for communication with a proximal end of the elongate body;
a retention balloon spaced proximally from the drainage aperture along the length of the elongate body;
tissue approximating structure extendable from the elongate body spaced proximally from the retention balloon along the length of the elongate body;
an actuating mechanism extending from the proximal end of the elongate body and comprising at least one tissue approximating structure control mechanism capable of actuating the at least one tissue approximating structure separately from the retention balloon; and
a protective enclosure comprising:
a first body portion moveably attached to a second body portion by a hinge connector, wherein the first and second body portions each comprise an inner compartment;
an open position in which the actuating mechanism is manipulatable for actuation of the at least one tissue approximating structure; and
a closed position in which the first and second body portions have been rotated toward each other about the hinge connector to create the protective enclosure that surrounds at least a portion of the actuating mechanism and prevents actuation of the at least one tissue approximating structure;
wherein the retention balloon, the tissue approximating structure, and the elongate body are positioned outside the protective enclosure when the protective enclosure is in its closed position.

2. The anastomosis device of claim 1, wherein the protective enclosure in its closed position comprises an inner cavity that comprises the inner compartments of the first and second body portions.

3. The anastomosis device of claim 1, wherein the protective enclosure surrounds the at least one tissue approximating structure control mechanism.

4. The anastomosis device of claim 1, further comprising a closure mechanism for maintaining the protective enclosure in a closed position.

5. The anastomosis device of claim 4, wherein the closure mechanism comprises a positive mechanical engagement between the first body portion of the protective enclosure and the second body portion of the protective enclosure.

6. The anastomosis device of claim 4, wherein the closure mechanism comprises a magnetic attraction element between the first body portion of the protective enclosure and the second body portion of the protective enclosure.

7. The anastomosis device of claim 1, wherein the protective enclosure comprises a relatively rigid outer surface surrounding an inner cavity, wherein at least a portion of the actuating mechanism is positioned within the inner cavity of the protective enclosure.

8. The anastomosis device of claim 1, wherein the protective enclosure comprises a flexible material that is conformable to at least some of the outer surfaces of the actuating mechanism.

9. The anastomosis device of claim 8, wherein the flexible material is elastically deformable.

10. The anastomosis device of claim 1, wherein the protective enclosure further comprises a locking mechanism.

11. The anastomosis device of claim 1, wherein the protective enclosure comprises a single piece of material.

12. The anastomosis device of claim 1, wherein the protective enclosure comprises at least one molded piece of material.

13. The anastomosis device of claim 12, wherein the protective enclosure comprises two separate pieces of material.

14. The anastomosis device of claim 1, wherein the tissue approximating structure comprises one or more movable elongate tines.

15. A protective enclosure at least partially surrounding an actuating mechanism that is operatively connected to tissue approximating structure of an anastomosis surgical device, wherein the anastomosis device comprises an elongate body having a drainage aperture at a distal end for communication with a proximal end of the elongate body, a retention balloon spaced from the drainage aperture along the length of the elongate body, and tissue approximating structure extendable from the elongate body and spaced proximally from the retention balloon along the length of the elongate body, wherein the actuating mechanism extends from a proximal end of the elongate body and comprises at least one tissue approximating structure control mechanism, and wherein the protective enclosure comprises a first body portion moveably attached to a second body portion by a hinge connector, wherein the first and second body portions each comprise an inner compartment, an open position in which the actuating mechanism is manipulatable for actuation of the at least one tissue approximating structure, and a closed position in which the first and second body portions have been rotated toward each other about the hinge connector to create the protective enclosure that surrounds at least a portion of the actuating mechanism and prevents actuation of the at least one tissue approximating structure control mechanism, and wherein the retention balloon, the tissue approximating structure, and the elongate body are positioned outside the protective enclosure when the protective enclosure is in its closed position.

16. The protective enclosure of claim 15, wherein the first and second body portions are moveable relative to each other.

17. The protective enclosure of claim 15, further comprising a retention balloon actuation mechanism.

18. The protective enclosure of claim 17, wherein the retention balloon actuation mechanism is positioned outside of the protective enclosure.

19. An anastomosis surgical device comprising:
an elongate body having a drainage aperture at a distal end for communication with a proximal end of the elongate body;
a retention balloon spaced proximally from the drainage aperture along the length of the elongate body;
tissue approximating structure extendable from the elongate body and spaced proximally from the retention balloon along the length of the elongate body;
a first actuating mechanism extending from the elongate body and comprising at least one retention balloon control mechanism;
a second actuating mechanism extending from the proximal end of the elongate body and comprising at least one tissue approximating structure control mechanism; and
a protective enclosure comprising:
a first body portion moveably attached to a second body portion by a hinge connector, wherein the first and second body portions each comprise an inner compartment;
an open position in which the second actuating mechanism is manipulatable for actuation of the at least one tissue approximating structure control mechanism; and
a closed position in which the first and second body portions have been rotated toward each other about the hinge connector to create the protective enclosure that surrounds at least a portion of the second actuating mechanism and prevents actuation of the second actuating mechanism;
wherein the retention balloon, the tissue approximating structure, and the elongate body are positioned outside the protective enclosure when the protective enclosure is in its closed position.

* * * * *